United States Patent [19]

Sichert

[11] 4,104,373

[45] Aug. 1, 1978

[54] THERAPEUTICAL COMPOSITION

[76] Inventor: Richard Sichert, Schneckenburger Strasse 42 8 Munich 80, Fed. Rep. of Germany

[21] Appl. No.: 360,935

[22] Filed: May 16, 1973

Related U.S. Application Data

[63] Continuation-in-part of Ser. No. 43,947, Jun. 5, 1970, abandoned.

[30] Foreign Application Priority Data

Jun. 20, 1969 [DE] Fed. Rep. of Germany ....... 1931467
Dec. 19, 1969 [DE] Fed. Rep. of Germany ....... 1963706

[51] Int. Cl.$^2$ .................... A61K 35/78; A61K 31/22; A61K 47/00
[52] U.S. Cl. ................................. 424/195; 424/312; 424/365
[58] Field of Search .......................................... 424/195

[56] References Cited

FOREIGN PATENT DOCUMENTS 1,963,706  6/1971  Fed. Rep. of Germany.
1,931,467  12/1970  Fed. Rep. of Germany.

OTHER PUBLICATIONS

Lyons, "Plant Names Scientific and Popular," p.101, Nelson, Baker & Co., Publishers; Detroit 1900.
Wren, "Potters Cyclopaedia of Botanical Drugs and Preparations," pp. 10, 11, 22, 26–27, 29–30, 50, 99, 120, 141–142, 155–156, 164, 166, 168–170, 207, 209, 225, 227, 336–337, 360, 364; London 1950.
Agriculture Handbook 172, pp. 7, 15, 19–20, 23–24, 28–29, U.S. Dept. Ag., Apr. 1960.
Published prospectus of "Unguentum ® Lymphaticum".

*Primary Examiner*—Donald B. Moyer
*Attorney, Agent, or Firm*—Watts, Hoffmann, Fisher & Heinke Co.

[57] ABSTRACT

Therapeutical compositions useful against congestions in the lymphatic system and comprising alkaloid-containing and/or glycoside-containing extracts of Umbelliferae, Liliaceae, Berberidaceae and Solanaceae plants and of Digitalis, Strophanthus, Convallaria or Crataegus plants and including the alkaloids, glycosides and salts of those plants.

11 Claims, No Drawings

THERAPEUTICAL COMPOSITION

This application is a continuation-in-part of my copending application Ser. No. 43,947, filed Jun. 5, 1970, now abandoned.

A remarkable increase of the therapy-resistant diseases is not to be doubted.

BACKGROUND OF THE INVENTION

While in case of the treatment of diseases of the blood-circulation numerous efficient remedies are available to the physician there is a sensible need of a remedy which efficiently removes the pathologic changes in the lymphatic system including its filtering mechanisms in the lymphatic ganglions. Particularly the activity of the known remedies against congestions of the lymphatic system is too low and slow and they have deleterious secondary effects.

The object of the present invention is to provide a remedy against congestions Colchicum the lymphatic system which acts more strongly and more rapidly without having deleterious secondary effects.

SUMMARY OF THE INVENTION

According to the invention the present object is achieved by a basic composition of matter to which one or more of several compositions may be added. The basic composition comprises a mixture of extracts of the Umbelliferae, Liliaceae, Berberidaceae and Solanaceae families of plants and an extract of a plant which has curative or tonic effects on the heart. Additional compositions which may be added to that basic composition include extracts of Calendulae, Taraxaci, Lactuca virosa, Hydrastis canadensis or Arum triphyllum, arsenic compounds, rectified petroleum, an ointment base, linoleic or linolenic acid in combination with a sulphur-containing amino acid and the biocatalyzer cytochrome C, pilocarpine and a preservative such as a compound of parahydroxybenzoic acid.

The invention also comprises remedies, particularly against congestions in the lymphatic system, containing the above constituents.

DETAILED DESCRIPTION OF THE INVENTION

The compositions according to the present invention involve the important technical advance as compared to the remedies of the prior art that they have a much more powerful and rapid action against congestions of the lymphatic system without deleterious secondary effects. Lymphatic congestions are the cause of many diseases. The mixtures according to the invention have a superior activity against these congestions. They are also applicable prophylactically. By regularly applying them the clogged lymphatic vessels and lymphatic clefts are drained to such an extent that a normalization of the lymph current in the vessels and tissue clefts is recovered. In such a way the lymphatic congestions, the swelling of tissues and indurations as well as the dolor sundromes connected with them disappear in a short time more or less depending on the severity of the case.

It has been found by experiments that the removal of the lymphatic congestions in therapy-resistant cases cannot be achieved by one, two or three of the ingredients of the composition. Accordingly, there is a true synergetic effect.

The superior activity of the compositions according to the invention and the absence of deleterious secondary effects when applying them has been proved by extensive clinical experiments carried out in the sanatorium of Professor Dr. Schedel in Kellberg bei passau, Germany.

According to a particular embodiment of the invention the composition is an ointment comprising a mixture of an extract of Umbelliferae, preferably an extract of *Conium maculatum, Cicuta virosa, Aethusa cynapium* or *Oenanthe crocata*, an extract of Liliaceae, preferably an extract of Colchicum autumnale, Veratrum album, Aloe or Asparagi, an extract of a plant selected from the group of plants consisting of Digitalis, Strophanthus, Convallaria and Cratageus, an extract of Berberidaceae, preferably an extract of Podophylli or Berberis vulgaris, an extract of Solanaceae, preferably an extract of Hyoscyami, *Atropa belladonna*, Mandragorae or *Datura stramonium*, and rectified, i.e., purified, petroleum as well as active ingredients for the cellular respiration, as an ointment-base. Owing to its high diffusibility the healing ointment according to the invention rapidly penetrates from the dermal periphery into the subcutaneous and interstitial tissue of the organs. This is achieved without encumbering the stomach and the intestine.

In the compositions according to the invention as extracts of Umbelliferae those of Conium maculatum and conium-like plants, as extracts of Liliaceae those of Colchici and colchicum-like plants, as extracts of Berberidaceae those of Podophylli and podophyllum-like plants and as extracts of Solanaceae those of Hyoscyami and hyoscyamus-like plants are particularly favorable.

According to the invention compositions which have curative or tonic effects on the heart are also present in the mixture preferably as extracts or tinctures of Digitalis, Strophanthus, Convalleria and Crataegus.

Preferred ratios of the amounts of the extract of Umbelliferae : extract of Liliaceae : extract of a plant effective on the heart : extract of Berberidaceae : extract of Solanaceae are about 4 to 12 : 2.8 to 9 : 2 to 6.5 : 2 to 6 : 2 to 7.5.

According to a convenient embodiment of the invention the composition also contains an extract of Calendulae, an extract of Taraxaci or an extract of Lactuca virosa. Thereby an increased effect is achieved. The composition according to the invention favorably also may contain rectified petroleum (oleum petrae rectificatum) by which in many cases a more rapid activity is attainable.

According to a particular embodiment of the invention the composition also contains arsenicum or compounds of arsenicum. By this means an additional very important enhancement of the activity is achieved. Examples of arsenicum or of arsenicum compounds which may be contained in the compositions according to the invention are from about 0.03 to about 0.35%, and in ointments preferably about 0.04 to about 0.06% of arsenicum or arsenicum compounds and from about 3 to about 35% of a 1% solution of potassium arsenite, preferably from about 4 to 6% in ointments.

According to a further favorable embodiment of the invention the composition also contains from about 0.2 to about 7%, and in ointments preferably from about 0.5 to about 2% of pilocarpine in the form of pilocarpine hydrochloride.

According to a special embodiment of the invention additionally materials of organ-specific activity may be contained in the composition. These are selected according to the organ where it is desired to obtain the main effect and may consist of from about 0.2 to about 35% of an extract of Hydrastis canadensis, preferably from about 2 to 3% in ointments, or from about 0.1 to about 1%, preferably from about 3 to about 5% in ointments of an extract of Arum triphyllum.

The compositions according to the invention may be used in allopathic or homeopathic forms and in fact by every mode of application, such as for oral, rectal or parenteral applications including the intravaginal application.

Suitable forms of preparations of the compositions according to the invention are, for example, capsules, suppositories, solvents and ointments. The preparations different from ointments may be prepared with or without an ointment base.

A preferred ointment according to the invention comprises an extract of Conium maculatum, an extract of Colchicum autumnale, an extract of Digitalis or Strophanthus, an extract of Podophylli, an extract of Hyoscyami, an extract of Calendulae and rectified petroleum as well as an ointment-base. It is particularly preferred that the ointment according to the invention contains from about 4.0 to 12.0% of an extract of Conium maculatum,
from about 2.8 to 9.0% of an extract of Colchicum autumnale,
from about 2.0 to 6.5% of an extract of Digitalis,
from about 2.0 to 6.0% of an extract of Podophylli,
from about 2.0 to 7.5% of an extract of Hyoscyami,
from about 1.2 to 4.0% of an extract of Calendulae and
from about 8.0 to 10.0% of rectified petroleum.

In case of using an extract of Strophanthus instead of Digitalis, the preferred proportion of it is from about 2.0 to 4.0%.

The preferred active ingredient of vital necessity for the cellular respiration is from about 76.1 to about 83.3% of an ointment base containing linoleic acid or linolenic acid in combination with a sulphur-containing amino acid and the biocatalyzer cytochrome C.

Further the composition according to the invention also may contain a preservative, such as an ester of parahydroxybenzoic acid and/or a salt thereof.

The ointment according to the invention also may contain perfumes.

Following are examples, illustrative of, but in no way intended to limit the present invention.

In the examples, the symbol DAB VI identifies 6 Edition 1926 of the German Pharmacopea which bears the name Deutsches Arzneibuch published in 1926 and revised in 1951 and a supplement thereto. Selected pages of that book describing the preparation of extracts, tinctures and essences in general and those particularly referred to herein and translations thereof are on file in my original application, Serial No. 43,947 of which this application is a continuation-in-part.

Parts of other German publications including *Chemie Lexikon*, *Phylotherapy* by Josef Karl and *Homeopathisches Arzneibuch* (HAB) and translations of each of these documents are also on file in said original application.

The preparation of extrcts beneficial to the heart are set out in *Potter's Cyclopedia* and the *American Handbook* No. 172 of April 1960, both of record in said original application.

EXAMPLE 1

The following ingredients were mixed:

| | | |
|---|---|---|
| an extract of Conium maculatum DAB VI | 4.2 | g |
| an extract of Colchicum autumnale DAB VI | 3.0 | g |
| an extract of Digitalis DAB VI | 2.1 | g |
| an extract of Podophyllum peltatum DAB VI | 2.1 | g |
| an extract of Hyoscyami DAB VI | 2.1 | g |
| an extract of Calendulae | 1.4 | g |
| rectified petroleum | 8.8 | g |
| | 23.7 | g |
| preservative, such as an ester of para-hydroxybenzoic acid | 0.2 | g |
| ointment base | 76.1 | g |
| | 100.0 | g |

The so prepared ointment was used for the removal of the lymphatic congestions without delerteious secondary effects having been observed. In severe and desolate cases the effect was enhanced by approximately doubling or trebling the above amounts of active ingredients with the exception of the rectified petroleum.

EXAMPLE 2

The following ingredients were mixed:

| | | |
|---|---|---|
| an extract of Conium maculatum DAB VI | 4.2 | g |
| an extract of Colchicum autumnale DAB VI | 3.0 | g |
| an extract of Strophanthus DAB VI | 2.1 | g |
| an extract of Podophyllum peltatum DAB VI | 2.1 | g |
| an extract of Hyoscyami DAB VI | 2.1 | g |
| an extract of Calendulae | 1.4 | g |
| rectified petroleum | 8.8 | g |
| | 23.7 | g |
| preservative, such as an alkali salt of the ethylester of para-hydroxybenzoic acid | 0.2 | g |
| ointment base | 76.1 | g |
| | 100.0 | g |

The so prepared ointment was used for the removal of the lymphatic congestions without deleterious secondary effects having been observed. In severe and desolate cases the effect was enhanced by approximately doubling or trebling the above amounts of active ingredients with the exception of rectified petroleum.

EXAMPLE 3

The following ingredients were mixed:

| | | |
|---|---|---|
| an extract of Conium maculatum DAB VI | 4.2 | g |
| an extract of Colchicum autumnale DAB VI | 3.0 | g |
| an extract of Digitalis DAB VI | 2.1 | g |
| an extract of Podophyllum peltatum DAB VI | 2.1 | g |
| an extract of Hyoscyami DAB VI | 2.1 | g |
| an extract of Calendulae | 1.4 | g |
| rectified petroleum | 8.8 | g |
| | 23.7 | g |
| ointment base | 76.3 | g |
| | 100.0 | g |

The mixture was filled into capsules, that is 0.3 g per capsule. For one cure 20 capsules were used at a daily dose of 1 capsule. It was observed that the lymphatic congestions were removed without deleterious secondary effects.

EXAMPLE 4

The following ingredients were mixed:

| | | |
|---|---|---|
| an extract of Conium maculatum DAB VI | 4.2 | g |
| an extract of Colchicum autumnale DAB VI | 4.0 | g |

-continued

| | | |
|---|---|---|
| an extract of Digitalis DAB VI | 2.1 | g |
| an extract of Podophyllum peltatum DAB VI | 2.1 | g |
| an extract of Hyoscyami DAB VI | 4.1 | g |
| an extract of Calendulae | 1.4 | g |
| | 17.9 | g |
| ointment base | 82.1 | g |
| | 100.0 | g |

Then the mixture was worked up with a suppository vehicle composition into suppositories per each suppository 0.3 g of the mixture and 1.7 g of the suppository vehicle composition having been used. For one cure 20 suppositiories were used at a daily dose of 1 suppository. The effects observed were similar to those in Example 3.

EXAMPLE 5

The following ingredients wer mixed:

| | | |
|---|---|---|
| an extract of Conium maculatum DAB VI | 4.2 | g |
| an extract of Colchicum autumnale DAB VI | 3.0 | g |
| an extract of Digitalis DAB VI | 2.1 | g |
| an extract of Podophyllum peltatum DAB VI | 2.1 | g |
| an extract of Hyoscyami DAB VI | 2.1 | g |
| an extract of Calendulae | 1.4 | g |
| rectified petroleum | 8.8 | g |
| | 23.7 | g |
| ointment base | 76.3 | g |
| | 100.0 | g |

Then from 5 to 10 g of this mixture were dissolved in 50 g of an ethereal oil, for example, a mixture of camphor, oil of turpentine, menthol and guaiacol oil. This solution was used for inhalations.

EXAMPLE 6

The following ingredients were mixed:

| | | |
|---|---|---|
| an extract of Conium maculatum DAB VI | 4.2 | g |
| an extract of Colchicum autumnale DAB VI | 4.0 | g |
| an extract of Digitalis DAB VI | 2.1 | g |
| an extract of Podophyllum peltatum DAB VI | 2.1 | g |
| an extract of Hyoscyami DAB VI | 4.1 | g |
| | 16.5 | g |
| preservative, such as an ester of para-hydroxybenzoic acid | 0.2 | g |
| ointment base | 83.3 | g |
| | 100.0 | g |

The so prepared ointment was used for the removal of the lymphatic congestions without deleterious secondary effects having been observed.

EXAMPLE 7

Example 3 was repeated except that in place of the extract of Digitalis DAB VI the same amount of an extract of Convallaria DAB VI was used. The effects achieved were similar to those in Example 3.

EXAMPLE 8

The following ingredients were mixed:

| | | |
|---|---|---|
| an extract of Conium maculatum DAB VI | 4.0 | g |
| an extract of Colchicum autumnale DAB VI | 2.8 | g |
| an extract of Strophanthus DAB VI | 2.0 | g |
| an extract of Podophyllum peltatum DAB VI | 2.8 | g |
| an extract of Hyoscyami DAB VI | 2.0 | g |
| an extract of Calendulae | 1.4 | g |
| | 15.0 | g |

The mixture ws filled into capsules, that is 0.5 g per capsule. It was applied perorally at a daily dose of one capsule for the removal of the lymphatic congestions without deleterious secondary effects having been observed.

EXAMPLE 9

The following ingredients were mixed:

| | | |
|---|---|---|
| an extract of Conium maculatum DAB VI | 4.2 | g |
| an extract of Colchicum autumnale DAB VI | 3.0 | g |
| an extract of Digitalis DAB VI | 2.1 | g |
| an extract of Podophyllum peltatum DAB VI | 2.1 | g |
| an extract of Hyoscyami DAB VI | 2.1 | g |
| an extract of Calendulae | 1.4 | g |
| rectified petroleum | 8.8 | g |
| | 23.7 | g |
| ointment base | 76.3 | g |
| | 100.0 | g |

Then 30 g of this mixture were mixed with 7.5 g of potassium arsenite (Fowler's solution, liquor kalii arsenicosi). The thus obtained mixture was filled into capsules, that is 0.3 g per capsule. The removal of the lymphatic congestions occurred substantially still more rapidly than by the mixture of Example 3 likewise no deleterious secondary effects having been observed.

EXAMPLE 10

The following ingredients were mixed:

| | | |
|---|---|---|
| coniine | 3.0 | g |
| colchicine | 2.0 | g |
| digitoxin | 0.1 | g |
| podophyllin | 0.8 | g |
| hyoscyamine | 5.0 | g |
| | 10.9 | g |

The mixture was filled into capsules, that is 0.09 g per capsule. Also in this case on peroral application at a daily dose of 1 capsule generally in a short time the removal of the lymphatic congestions without deleterious secondary effects was observed.

EXAMPLE 11

The following ingredients were mixed:

| | |
|---|---|
| coniine hydrobromide | 0.002 g |
| colchicine hydrochloride | 0.002 g |
| digitoxin sulphate | 0.0001 g |
| podophyllin hydrobromide | 0.001 mg |
| hyoscyamine hydrobromide | 0.005 g |

The mixture was dissolved in a sterilized physiological salt solution and filled into ampules and injected intravenously or subcutaneously. Also in this case generally a quick removal of the lymphatic congestions without deleterious secondary effects was observed.

EXAMPLE 12

The following ingredients were mixed:

| | | |
|---|---|---|
| an extract of Circuta virosa DAB VI | 5.0 | g |
| an extract of Aloe DAB VI | 4.5 | g |
| an extract of Digitalis DAB VI | 2.1 | g |
| an extract of Berberis vulgaris DAB VI | 2.8 | g |
| an extract of Atropa belladonna DAB VI | 4.1 | g |
| an extract of Calendulae | 1.8 | g |
| | 20.3 | g |
| preservative, such as an ester of para-hydroxybenzoic acid | 0.2 | g |

-continued

| | | |
|---|---|---|
| ointment base | 79.5 | g |
| | 100.0 | g |

The so prepared ointment was used for the removal of the lymphatic congestions without deleterious secondary effects having been observed.

EXAMPLE 13

The following ingredients were mixed:

| | | |
|---|---|---|
| an extract of Aethusa cynapium DAB VI | 5.0 | g |
| an extract of Asparagi DAB VI | 4.5 | g |
| an extract of Crataegus DAB VI | 2.1 | g |
| an extract of Podophyllum peltatum DAB VI | 2.8 | g |
| an extract of Mandragorae DAB VI | 4.1 | g |
| an extract of Taraxaci | 1.8 | g |
| | 20.3 | g |
| preservative, such as an ester of para-hydroxybenzoic acid | 0.2 | g |
| ointment base | 79.5 | g |
| | 100.0 | g |

The so prepared ointment was used for the removal of the lymphatic congestions and the effects observed were similar to those in Example 12.

EXAMPLE 14

The following ingredients were mixed:

| | | |
|---|---|---|
| an extract of Oenanthe crocata DAB VI | 5.0 | g |
| an extract of Veratrum album DAB VI | 4.5 | g |
| an extract of Strophanthus DAB VI | 2.1 | g |
| an extract of Podophyllum peltatum DAB VI | 2.8 | g |
| an extract of Datura stramonium DAB VI | 4.1 | g |
| an extract of Lactuca virosa | 1.8 | g |
| | 20.3 | g |
| preservative, such as an ester of para-hydroxybenzoic acid | 0.2 | g |
| ointment base | 79.5 | g |
| | 100.0 | g |

The so prepared ointment was used for the removal of the lymphatic congestions and the effects observed were similar to those in Example 12.

EXAMPLE 15

The following ingredients were mixed:

| | | |
|---|---|---|
| an extract of Conium maculatum DAB VI | 4.3 | g |
| an extract of Asparagi DAB VI | 2.8 | g |
| an extract of Crataegus DAB VI | 2.1 | g |
| an extract of Podophyllum peltatum DAB VI | 2.8 | g |
| an extract of Hyoscyami DAB VI | 2.0 | g |
| | 14.0 | g |

The mixture was filled into capsules, that is 0.05 g per capsule. It was applied perorally at a daily dose of one capsule for the removal of the lymphatic congestions without deleterious secondary effects having been observed.

Although the present invention has been described with reference to particular embodiments and examples, it will be apparent to those skilled in the art that variations and modifications of this invention can be made without departing from the principles and true spirit of the invention.

What is claimed is:

1. A composition of matter for treating lymphatic congestions comprising a mixture of:
   (a) an extract of an Umbelliferae selected from the group consisting of *Conium maculatum, Cicuta virosa, Aethusa cynapium* and *Oenanthe crocata,*
   (b) an extract of a Liliaceae selected from the group consisting of *Colchicm autumnale, Veratrum album,* Aloe and Asparagi,
   (c) an extract of a plant selected from the group consisting of Digitalis, Strophanthus, Convallaria and Crataegus,
   (d) an extract of a Berberidaceae selected from the group consisting of Podophylli and *Berberis vulgaris,* and
   (e) an extract of a Solanaceae selected from the group consisting of Hyoscyami, *Atropa belladonna,* Mandragorae and *Datura stramonium,*
   the ratios of extracts (a), (b), (c), (d) and (e) present being, respectively, about 4 to 12 : about 2.8 to 9 : about 2 to 6.5 : about 2 to 6 : about 2 to 7.5.

2. The composition of matter set forth in claim 1 comprising the mixture of claim 2 and between about 1.2 and 4.0% of an extract of a plant selected from the group consisting of Calendulae, Taraxaci and *Lactuca virosa.*

3. The composition of matter comprising the mixture of extracts set forth in claim 1 and between about 8.0 and about 10.0% of rectified petroleum.

4. The composition of matter set forth in claim 1 comprising a mixture of from about 4.0 to about 12.0% of an extract of Conium maculatum, from about 2.8 to about 9.0% of an extract of Colchicum autumnale, from about 2.0 to 4.0% of an extract of Strophanthus, from about 2.0 to about 6.0% of an extract of Podophylli, from about 2.0 to about 7.5% of an extract of Hyoscyami, and from about 1.2 to about 4.0% of an extract of Calendulae.

5. The composition of matter comprising the mixture of extracts set forth in claim 1 and between about 0.2 and about 35% of an extract of *Hydrastis canadensis.*

6. The composition of matter comprising the mixture of extracts set forth in claim 1 and between about 0.1 to about 5% of an extract of *Arum triphyllum.*

7. The composition of matter comprising the mixture of extracts set foth in claim 1 and between about 0.2 and about 7% of pilocarpine.

8. The composition of matter comprising the extracts set forth in claim 1 and about 0.2 g of the ethyl ester of para-hydroxybenzoic acid.

9. The composition of matter set forth in claim 1 comprising a mixture of from about 4.0 to about 12.0% of an extract of *Conium maculatum,* from about 2.8 to about 9.0% of an extract of *Colchicum autumnale,* from about 2.0 to about 6.5% of an extract of Digitalis, from about 2.0 to about 6.0% of an extract of Podophylli, from about 2.0 to about 7.5% of an extract of Hyoscyami, and from about 1.2 to about 4.0% of an extract of Calendulae.

10. The composition of matter comprising the mixture of extracts set forth in claim 9 and between about 8.0 and about 10.0% of rectified petroleum.

11. The composition of matter comprising the extracts set forth in claim 10 and about 0.2 g of the ethyl ester of para-hydroxybenzoic acid.

* * * * *

UNITED STATES PATENT AND TRADEMARK OFFICE
CERTIFICATE OF CORRECTION

PATENT NO. : 4,104,373
DATED : August 1, 1978
INVENTOR(S) : Richard Sichert

It is certified that error appears in the above-identified patent and that said Letters Patent are hereby corrected as shown below:

Column 1, line 20, "Colchicum" should be -- of --.

Column 2, line 5, "passau" should be -- Passau --;
          line 15, "Cratageus" should be -- Crataegus --.

Column 3, line 65, "extrcts" should be -- extracts --.

Column 4, line 17, "delerteious" should be -- deleterious --.

Column 5, line 19, "wer" should be -- were --.

Column 6, line 1, "ws" should be -- was --.

Column 8, line 7 (Claim 1) "Colchicm" should be
          -- Colchicum --;
          line 22 (Claim 2) "2" should be -- 1 --.

Signed and Sealed this

Sixth Day of March 1979

[SEAL]

Attest:

RUTH C. MASON
Attesting Officer

DONALD W. BANNER
Commissioner of Patents and Trademarks